(12) United States Patent
Shah et al.

(10) Patent No.: US 11,666,535 B2
(45) Date of Patent: Jun. 6, 2023

(54) CURCUMINOID COMPOSITES

(71) Applicant: INVENTIA HEALTHCARE LIMITED, Mumbai (IN)

(72) Inventors: Vaibhavi Shah, Mumbai (IN); Vijayendrakumar Redasani, Thane (IN); Shajahan Abdul, Madurai (IN); Vishal Shah, Mumbai (IN); Rajat Shah, Mumbai (IN)

(73) Assignee: INVENTIA HEALTHCARE LIMITED, Mumbai (IN)

( * ) Notice: Subject to any disclaimer, the term of this patent is extended or adjusted under 35 U.S.C. 154(b) by 0 days.

(21) Appl. No.: 17/271,498

(22) PCT Filed: Sep. 25, 2019

(86) PCT No.: PCT/IB2019/058124
§ 371 (c)(1),
(2) Date: Feb. 25, 2021

(87) PCT Pub. No.: WO2020/065548
PCT Pub. Date: Apr. 2, 2020

(65) Prior Publication Data
US 2021/0330591 A1    Oct. 28, 2021

(30) Foreign Application Priority Data

Sep. 26, 2018 (IN) .............................. 201821036345

(51) Int. Cl.
| | |
|---|---|
| *A61K 9/14* | (2006.01) |
| *A61K 31/047* | (2006.01) |
| *A61K 31/05* | (2006.01) |
| *A61K 31/715* | (2006.01) |
| *A61K 36/899* | (2006.01) |
| *A61K 36/906* | (2006.01) |
| *A61K 36/9066* | (2006.01) |
| *A23L 33/105* | (2016.01) |
| *A23L 33/125* | (2016.01) |

(52) U.S. Cl.
CPC ............ *A61K 9/141* (2013.01); *A23L 33/105* (2016.08); *A23L 33/125* (2016.08); *A61K 9/145* (2013.01); *A61K 9/146* (2013.01); *A61K 9/148* (2013.01); *A61K 31/047* (2013.01); *A61K 31/05* (2013.01); *A61K 31/715* (2013.01); *A61K 36/899* (2013.01); *A61K 36/906* (2013.01); *A61K 36/9066* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 9,119,411 B2 * | 9/2015 | Zasypkin | ................ A23P 10/30 |
| 9,801,855 B2 | 10/2017 | Bansal et al. | |
| 2013/0303628 A1 | 11/2013 | Breitenbach et al. | |
| 2015/0024060 A1 | 1/2015 | Madhavi et al. | |
| 2016/0151440 A1 | 6/2016 | Gopi | |
| 2016/0256412 A1 | 9/2016 | Majeed et al. | |
| 2021/0227862 A1 * | 7/2021 | Van Den Berg | ........ A23L 19/01 |
| 2022/0054580 A1 * | 2/2022 | Ran | ..................... A61K 9/1075 |

FOREIGN PATENT DOCUMENTS

| | | | |
|---|---|---|---|
| WO | WO-2011125070 A2 | 10/2011 | |
| WO | WO-2016083874 A1 | 6/2016 | |
| WO | WO-2018211380 A1 * | 11/2018 | ............. A61K 31/12 |
| WO | WO-2021001860 A1 * | 1/2021 | |

OTHER PUBLICATIONS

International Search Report issued in PCT/IB2019/058124 dated Nov. 25, 2019.
Ai Mey Chuah et al; "Enhanced bioavailability and 1-11 bioefficacy of an amorphous solid dispersion of curcumin"; Food Chemistry; vol. 156, pp. 227-233; Aug. 2014 *Whole document especially abstract and para 2.2*.
A. Gangurde and P. Amin; "Enhancement of 1-11 Solubility and Dissolution Rate of Curcumin by Eudragit Epo-based Solid Dispersions Prepared by Hot Melt Extrusion and Spray Drying Technology"; Conference Paper: European Conferences on Pharmaceutics; Apr. 2015 *Abstract*.

* cited by examiner

*Primary Examiner* — Sin J Lee
(74) *Attorney, Agent, or Firm* — Blank Rome LLP

(57) ABSTRACT

The present invention relates to a melt composite comprising one or more curcuminoids and a carrier selected from rice bran extract, mannitol, maltodextrin and mixtures thereof. The invention also provides a process for preparation of the melt composite, wherein the mixture of curcuminoids, rice bran extract, mannitol, maltodextrin and mixture thereof may be subjected to controlled conditions of heating and granulation. The melt composite may also be optionally comprised of one more excipient suitable for use for human consumption. Curcuminoid composites can be formulated in suitable solid, liquid or semisolid compositions. Curcuminoid composites and the compositions thereof, exhibit rapid dissolution and enhanced bioavailability.

7 Claims, No Drawings

CURCUMINOID COMPOSITES

This application is the U.S. national stage of International Patent Application No. PCT/IB2019/058124, filed Sep. 25, 2019, which claims priority to Indian Patent Application No. 201821036345, filed Sep. 26, 2018.

FIELD OF THE INVENTION

The present invention relates to a melt composite comprising one or more curcuminoids and a carrier selected from rice bran extract, mannitol, maltodextrin and mixtures thereof, said composite exhibiting rapid dissolution and enhanced bioavailability. The composite may optionally comprise an excipient commonly used in the pharmaceutical, nutraceutical or food industry.

The invention further provides a process for preparation of the melt composite, wherein one or more curcuminoids and the carrier selected from rice bran extract, mannitol, maltodextrin and mixtures thereof, may be subjected to controlled conditions of heating and granulation. The process as described herein is simple, yet effective, solvent-free process, which is industrially useful for preparation of curcuminoid composites with enhanced dissolution and bioavailability.

The composite, as described herein may be further formulated in solid, liquid and semisolid compositions, comprising one or more excipients suitable for the preparation. The compositions are useful for human and animal consumption in various applications such as joint health, brain health, skin and personal care, sports nutrition and liver health.

BACKGROUND OF THE INVENTION

Curcuminoids are diaryl heptanoid derivatives isolated from a member of the ginger family (Zingiberaceae). The three major curcuminoids present in Turmeric are: curcumin, desmethoxycurcumin, and bisdesmethoxycurcumin. Curcumin is the principal curcuminoid of Turmeric. Curcuminoids are polyphenols and are responsible for the yellow color of turmeric.

Curcuminoids have been suggested for a variety of therapeutic and prophylactic applications. For example, curcuminoids have a variety of biological activities and pharmacological actions, such as anti-cancer, anti-viral, anti-arthritic, anti-amyloid, antioxidant, anti-inflammatory, anti-obesity, anti-depressant, improves symptoms of neurodegenerative diseases like Parkinson's, Alzheimer's, and Huntington's, improves brain function/health, improving mental health, lowers the risk of brain and heart diseases, regulates cholesterol, lowers the risk of atherosclerosis, improves cardiovascular function, prevents blood clots, improves symptoms of inflammatory bowel disease, improves symptoms of gastrointestinal conditions like constipation/dyspepsia/gastric ulcers/ulcerative colitis/pancreatitis, prevents cystic fibrosis, reduces pain and soreness in post-surgical recovery, relieves symptoms of menstruation, lowers the risk of diabetes, promotes liver health, delays aging, promotes skin and ocular health, and benefits sports nutrition by lowering oxidative stress in muscles, enhancing recovery of and improving muscle performance, improving endurance capacity, improving resistance to fatigue, and improving joint mobility and function.

The therapeutic efficiency of curcuminoids is limited due to poor solubility in water (the maximum solubility is 11 ng/ml in aqueous buffer pH 5.0). Poor aqueous solubility and poor absorption, high pre-systemic metabolism in gastrointestinal tract (GIT), low stability due to degradation in GIT at neutral and alkaline pH, and rapid systemic metabolism to sulfate and glucuronide conjugates, translates into poor bioavailability of curcuminoids after oral delivery. It has been reported that serum levels in humans, even after an oral dose of 2 g curcumin alone, was either undetectable or very low.

Prior art discloses different techniques to solubilize curcuminoids.

US Patent Publication No. US 2013/0303628 A1 provides a melt-processed solid dispersion product comprising one or more curcuminoids, a thermoplastic polymer, and a phosphatide (like glycerophospholipids, phosphoglycerides, phosphatidylcholines, lecithin).

U.S. Pat. No. 9,801,855 B2 relates to a method of preparation of discrete particles of nanocrystalline solid dispersion, wherein said discrete particle comprises crystals of active ingredient(s) in a matrix of crystallization inducer(s) and/or coexisting with crystals of crystallization inducer(s), optionally along with excipient(s). An active ingredient and crystallization inducer is dissolved in a solvent or solvent mixture. The solvent is removed by vacuum drying, spray drying or freeze drying. Spray drying is the preferred method. Oral bioavailability studies of spray-dried curcumin-stearic acid (50:50) solid dispersions, after single oral dose (250 mg/kg) to female SD rats showed a $C_{max}$ of curcumin at 245.9 ng/ml and an $AUC_{0-\infty}$ of curcumin of 1156 ng/ml.

US Publication no. 2016/0256412 provides a method of solubilizing curcumin/curcuminoid mixtures using polyvinyl pyrrolidone (PVP) and dioctyl sulfosuccinate (AOT) (Docusate sodium), said method comprising steps of dissolving the curcuminoids, PVP and AOT in solvent such as ethanol, evaporating the solvent in a rota-evaporator, adding distilled water, filtering and spray drying.

US patent application 2016/0151440 relates to a composition which mainly consists of curcumin mixture and water extract. The curcumin mixture comprises curcumin dry crystals, volatile oil, fixed oil whereas water extract comprises soluble proteins, dietary fibers and carbohydrates extracted from turmeric. The composition also consists of a natural emulsifier isolated from an American tree *Quillaja saponaria* and lecithin.

EP patent 2555787 provides a composition of a curcuminoid mixture and added essential oil of turmeric, wherein the weight ratio of the curcuminoid mixture to the added essential oil of turmeric is 10:1, wherein the curcuminoid mixture includes curcumin, demethoxycurcumin and bisdemethoxycurcumin, and wherein the essential oil of turmeric includes 45% ar-turmerone. The invention relates to a formulation of curcuminoid with essential oil of turmeric to enhance the bioavailability of curcumin and to augment the biological activity of curcumin.

Prior art references mainly relate to use of organic solvents, synthetic polymers, emulsifiers or essential oils for enhancing the bioavailability of curcumin compositions. The efforts are also made to use hydrophilic cellulose polymers or other synthetic excipients in order to overcome poor solubility of curcumin.

However, there is still unmet need for use of alternate excipients obtained from natural source or development of simple but effective processes, so that the compositions would be acceptable and useful for nutraceutical, cosmetic and food applications.

The present invention provides melt composite comprising one or more curcuminoids and a carrier selected from rice bran extract, mannitol, maltodextrin and mixtures thereof, which is obtained from natural source. The melt composites comprising curcuminoids and natural carrier exhibit rapid dissolution and enhanced bioavailability. Such composites comprising of carriers and mixtures thereof are not reported till date in any published literature. The composites can be formulated in suitable solid, liquid or semisolid compositions by adding one or more excipients, acceptable in nutraceutical, pharmaceutical and food industry. The present invention provides a method of preparing said compositions using a simple, yet effective, solvent-free process.

OBJECTS OF THE INVENTION

Main object of the present invention is to provide melt composite comprising one or more curcuminoids, which exhibit rapid dissolution and enhanced bioavailability of the curcuminoid(s).

One important objective of the present invention is to provide melt composite comprising one or more curcuminoids and a carrier selected from rice bran extract, mannitol, maltodextrin and mixture thereof, which exhibit rapid dissolution of the curcuminoid (s).

Still one more important objective of the present invention is to provide melt composite comprising one or more curcuminoids and a carrier or mixture thereof obtained from natural source.

One more objective of the present invention is to provide melt composite comprising one or more curcuminoids and a carrier selected from rice bran extract, mannitol, maltodextrin and mixture thereof, which may be optionally further comprised of at least one excipient acceptable for use in pharmaceutical, cosmetic, nutraceutical or food industry.

Yet one more objective of the present invention is to provide melt composite comprising about 5 to 90% of one or more curcuminoids by weight of the composition.

One more objective of the invention is to provide melt composite comprising about 10 to 95% of the carrier by weight of the composition, selected from rice bran extract, mannitol, maltodextrin and the mixture thereof.

One objective of the present invention is to provide melt composite comprising curcuminoid (s) to carrier in the ratio varying from about 1:0.1 to 1:20.

Another objective is to provide a process for the preparation of the said melt composites, which is simple, yet cost effective and free of solvents.

One more important objective of the present invention is to provide a process for preparation of the melt composite, wherein one or more curcuminoids and carrier selected from rice bran extract, mannitol, maltodextrin and the mixture thereof, may be subjected to controlled conditions of heating and granulation.

One objective of the present invention is to provide curcuminoid melt composite, further optionally comprising one or more excipient which is acceptable in nutraceutical, pharmaceutical or food industry.

According to one more objective of this invention, the composite may further be formulated into curcuminoid compositions by employing excipients commonly used in the pharmaceutical, nutraceutical and food industry.

DETAILED DESCRIPTION OF THE INVENTION

It has surprisingly been found that melt composite of the present invention, comprising one or more curcuminoids and carrier selected from rice bran extract, mannitol, maltodextrin and mixture thereof, exhibit rapid dissolution and enhanced bioavailability of the curcuminoid(s). The carriers as used herein may be obtained from natural source. The composites may further optionally be comprised of at least one excipient acceptable for pharmaceutical, nutraceutical, cosmetic or food industry.

The present invention uses curcuminoid extract of *Curcuma* species of the Zingiberaceae (ginger) family.

The term 'curcuminoid extract' is used herein to mean the extract of roots, tubers or rhizomes of the *Curcuma* species of the Zingiberaceae (ginger) family including but not limited to species like *Curcuma longa, Curcuma amada, Curcuma angustifolia, Curcuma caesia, Curcuma zedoaria, Curcuma caulina, Curcuma aromatica, Curcuma wenyujin, Curcuma xanfhorrhiza, Curcuma phaeocaulis, Curcuma leucorrhiza* and *Curcuma kwangsiensis*.

The term 'curcuminoid' is used herein to mean curcumin (diferuloylmethane), desmethoxycurcumin, or bisdesmethoxycurcumin, including their polymorphs, hydrates, solvates, derivatives, and mixtures thereof. The curcuminoid may be obtained by natural or synthetic means.

The term 'melt composite' as used herein refers to a composition which exists as a combination of two or more components that results in better or enhanced properties than those of the individual components used alone. These properties can be related to performance of the product like dissolution, stability, bioavailability and the like. Such composition in present context can be prepared by specific process, using conditions of controlled heat treatment and granulation. The components in present invention are one or more curcuminoids, carrier selected from rice bran extract, mannitol, maltodextrin and mixture thereof, along with one or more excipient, which may be optionally added during the process of preparation. The carrier used in the composite is obtained from natural source.

The one or more curcuminoids in the composition may be in their crystalline form or in the amorphous form or as mixtures of crystalline and amorphous forms.

As per one embodiment of the invention, the present composition uses a curcuminoid extract containing at least 30% by weight of one or more curcuminoids. The curcuminoid content in the extract is preferably in the range of 30% to 100%, more preferably in the range of 50% to 95%, and most preferably in the range of 70% to 95% by weight of the extract.

As per one more embodiment of the invention, the curcuminoid(s) may be present in concentrations from 5% to 90% by weight of the composition. More preferably curcuminoids may be present in concentrations from 10 to 85% by weight of the composition.

According to one embodiment of the invention, the ratio of the curcuminoid(s) to carrier, in the melt composite ranges from about 1:0.1 to about 1:20 preferably from about 1:0.15 to about 1:15 and more preferably from about 1:0.2 to about 1:10.

In one of the embodiments of the present invention, the melt composite is comprised of about 10% to about 95% carrier by weight of the composition.

As per one embodiment of the present invention, the melt composite may be comprised of one or more curcuminoids and carrier selected from rice bran extract, mannitol, maltodextrin and mixture thereof.

As per still one more embodiment, the composite may be comprised of one or more curcuminoids and a mixture of rice bran and mannitol as a carrier.

According to one embodiment, the composite may be comprised of one or more curcuminoids and a mixture of rice bran extract and maltodextrin as a carrier.

According to still one more embodiment, the melt composite may preferably be comprised of one or more curcuminoids and a mixture of rice bran extract, mannitol and maltodextrin.

In one of the embodiments, the melt composite comprises rice bran extract at a concentration of about 10% to about 95% by the weight of the melt composite.

The rice bran extract generally contains varied concentrations of proteins, fats, and carbohydrates.

For example, one type of rice bran extract has protein content of about 13% to about 18%, fat content of about 15% to about 25% and carbohydrate content of about 40% to about 52%, when considered by weight of the extract.

Another type of rice bran extract has protein content of about 14% to about 20%, fat content of about 18% to about 21% and carbohydrate content of about 33% to about 40%, when considered by weight of the extract.

The fat content of the extract may vary from about 14% to about 18% for a full fat rice bran, about 3% to about 14% for low fat rice bran or less than about 3% for de-fatted rice bran.

Another type of rice bran extract may have protein content of about 12% to about 14%, fat content of about 15% to about 19% and carbohydrate content of 40% to about 45%, when considered by weight of the extract.

Other types of rice bran extract may have protein content of about 9% to about 13%, fat content of about 12% to about 18% and carbohydrate content of 64% to about 71%, when considered by weight of the extract.

Yet another type of rice bran extract may have protein content of about 8% to about 10%, fat content of about 6% to about 9% and carbohydrate content of 77% to about 82%, when considered by weight of the extract.

Yet another type of rice bran extract may have protein content of about 11% to about 15%, fat content of about 1% to about 20% and carbohydrate content of 34% to about 65%, when considered by weight of the extract.

The curcuminoid melt composites may comprise mixtures of rice bran extract and mannitol, wherein the ratio of the curcuminoid(s) to the said mixture ranges from 1:0.1 to 1:20.

As per one embodiment of the invention, the curcuminoid melt composites may comprise one or more curcuminoids, rice bran extract and mannitol, in the ratio ranging from 1:0.05:0.1 to 1:10:10 and preferably ranging from 1:0.1:0.2 to 1:8:9.

According to one embodiment, curcuminoid melt composite may comprise mixtures of rice bran extract and maltodextrin, wherein the ratio of the curcuminoid(s) to the said mixture ranges from 1:0.1 to 1:20.

The curcuminoid melt composites may comprise one or more curcuminoids, rice bran extract and maltodextrin, in the ratio ranging from 1:0.05:0.1 to 1:10:10 and preferably ranging from 1:0.1:0.2 to 1:8:9.

The melt composite may optionally be comprised of at least one more excipient selected from diluents, carriers, binders, disintegrants, lubricants, glidants, solubilizers, carriers, vehicles, stabilizers, buffers, preservatives, acidifiers, alkalizers, sorbents, antioxidants, complexing agents, viscosity enhancers, plasticizers, coating materials, sweeteners, colors, and flavors. The optional excipient may be intragranularly or extragranularly added in the melt composite.

As per one embodiment, the optional excipient comprised in the melt composite may be selected from the group of polysaccharide and polysaccharide hydrocolloids, but not limited to mucilages, glucans and gums such as acacia, tragacanth, karaya, xanthan gum, gellan gum, karaya gum, gum ghatti, Hibiscus mucilage, alginates, chitosan, carrageenan, pullulan, fucoidan, hyaluronan and the mixtures thereof;

sugar alcohols selected from, but not limited to xylitol, sorbitol, arabitol, erythritol, glycerol, isomalt, lactitol, maltitol;

Starch and starch sugars selected from, but not limited to corn starch, tapioca, arrowroot, and wheat, rice, and potato starches. glucose, dextrose, fructose, and the mixtures thereof;

The excipients which may be optionally used as per the invention can aid the processing of the melt composite to final granular or powder form. These excipients can be also selected from the group of, but not limited to silicon dioxide, citric acid and the like.

The melt composites of the present invention do not necessarily use surfactants to achieve the desired objective.

The melt composites of the present invention can be manufactured using the techniques such as melt granulation, melt extrusion, melt solidification, melt spray congealing and the like, wherein the components of the composite can be subjected to controlled conditions of heating, followed by granulation.

The compositions of the melt composites of the present invention may be tablets, effervescent tablets, orally-disintegrating tablets, mouth dissolving tablets, sublingual tablets, buccal tablets, capsules, pills, chewing gums, films, powders, granules, beads, pellets, lozenges, pastilles, softgels, jellies, semi-solid, pastes, syrups, elixirs, solutions, suspensions, dispersions, and emulsions and the like.

The melt composites can be formulated in suitable compositions by using one or more excipients acceptable in pharmaceutical, nutraceutical, cosmetics or food industry. The compositions comprising the said melt composites may be manufactured by conventional processes known to a person skilled in the art. The compositions are useful for human and animal consumption in various applications such as joint health, brain health, skin and personal care, sports nutrition and liver health.

The melt composites and their compositions are analyzed for their dissolution in accordance with the recommendation of Dietary Supplements Compendium (DSC) 2015, United States pharmacopeia (USP) using the following conditions: 900 ml of purified water containing 1% sodium lauryl sulphate, USP apparatus II (paddle) at 100 revolutions per minute, 37° C. The pharmacokinetics of curcuminoid melt composites of the present invention is studied in animal model and bioavailability study of curcuminoid composition filled in capsules is carried out in healthy volunteers in comparison to standard curcuminoid extract capsules, which is used as a reference formulation.

The invention is now illustrated with non-limiting examples.

Example 1

Curcuminoid extract (containing 95.4% curcuminoids) and mannitol SD 200, in ratios a) 1:0.25 and b) 1:0.5, were sifted through 20 mesh ASTM and mixed for 10 minutes to give a mixture. The mixture was subjected to hot melt extrusion using the conditions in Table 1, cooled, milled and sifted to give the melt composite.

TABLE 1

Hot melt extruder conditions for processing of example 1
Temperature of Chambers

| Chamber | Temperature (° C.) |
|---|---|
| 2 | 25 |
| 3 | 40 |
| 4 | 160 |
| 5 | 180 |
| 6 | 180 |
| 7 | 180 |
| 8 | 180 |
| Die Zone | 180 |

Extruder RPM = 75
Feeder RPM = 15

Physical Mixture (PM)

A physical mixture of curcuminoid extract (containing 95.4% curcuminoids) and mannitol SD 200, in a 1:1 ratio, was prepared by sifting the individual ingredients through 20 mesh ASTM and blending them for 10 minutes.

Dissolution Studies:

Curcuminoid extract 95.4% (active), melt composites of example 1a) and 1b), and physical mixture, all equivalent to 50 mg of curcuminoids, were analyzed for dissolution of curcuminoids at conditions mentioned earlier. The results of the same are given in Table 2.

TABLE 2

Dissolution of curcuminoid extract 95.4%, physical mixture,
and melt composites of examples 1a) and 1b)

| | % Cumulative Dissolution Profile | | | |
|---|---|---|---|---|
| Time (min) | Curcuminoid Extract | Physical Mixture (PM) | Melt Composite of Ex. 1a) | Melt Composite of Ex. 1b) |
| 15 | 18 | 17 | 88 | 91 |
| 30 | 27 | 23 | 93 | 94 |
| 45 | 33 | 29 | 93 | 95 |
| 60 | 38 | 33 | 94 | 95 |

* Ex. = Example; min = minutes

The dissolution data in table 2 shows:

At 15 minutes, melt composites of the present invention exhibit a dissolution of 88% and 91%, when compared to a mere 17%-18% for curcuminoid extract or physical mixture.

At 30 minutes, melt composites of the present invention exhibit a dissolution of greater than 90% while curcuminoid extract shows a dissolution of a mere 27% and physical mixture shows a dissolution of a mere 23%.

This clearly indicates that melt composites of the present invention exhibit a significantly higher rate and extent of dissolution, when compared to either curcuminoid extract or the physical mixture.

Example 2

Curcuminoid extract (containing 95.4% curcuminoids) (active) and rice bran extract (containing 14.16% protein, 16.48% fat and 51.61% carbohydrates), in a ratio of 1:5, were sifted through 20 mesh ASTM and mixed for 10 minutes to give a mixture. The mixture was subjected to hot melt extrusion using the conditions in Table 1, cooled, milled and sifted to give the melt composite.

Dissolution Studies:

Curcuminoid extract (95.4%) (active), and the melt composite, all equivalent to 50 mg of curcuminoids, were analyzed for dissolution of curcuminoids at conditions mentioned earlier. The results of the same are given in Table 3.

TABLE 3

Dissolution of curcuminoid extract 95.4%
and melt composite of example 2

| Time | % Cumulative Dissolution Profile | |
|---|---|---|
| (min) | Curcuminoid Extract | Melt Composite of Ex. 2 |
| 15 | 18 | 63 |
| 30 | 27 | 76 |
| 45 | 33 | 81 |
| 60 | 38 | 84 |

* Ex. = Example; min = minutes

The dissolution data in table 3 shows:

At 15 minutes, the melt composite of example 2 exhibits a dissolution of 63% when compared to a mere 18% for curcuminoid extract At 30 minutes, the melt composite of example 2 exhibits a dissolution of 76% when compared to a mere 27% for curcuminoid extract Table 3 clearly indicates that melt composite of the present invention exhibits a higher rate and extent of dissolution, when compared to curcuminoid extract.

Example 3

Curcuminoid extract containing 95.4% curcuminoids (42.08% w/w of composition), mannitol (SD 200) (21.04% w/w of composition), rice bran extract containing 14.16% protein, 16.48% fat and 51.61% carbohydrates (13.84% w/w of composition), and citric acid monohydrate (21.04% w/w of composition) and were sifted through 30 mesh ASTM and mixed for 10 minutes to give a mixture. The mixture was hot melt extruded using the conditions in Table 1, cooled, milled and sifted to give the melt composite. Colloidal silica (2.0% w/w of composition) was sifted through 40 mesh ASTM. The extrudates were blended with the sifted colloidal silica in a blender for 10 minutes to give the melt composite composition.

Physical Mixture (PM) of Example 3

A physical mixture of the melt composite of Example 3 was prepared by sifting the individual ingredients (curcuminoid extract, mannitol, rice bran extract, and citric acid) through 20 mesh ASTM and blending them for 10 minutes.

Example 4

Curcuminoid extract containing 95.4% curcuminoids (21.04% w/w of composition), mannitol (SD 200) (10.63% w/w of composition), rice bran extract containing 14.16% protein, 16.48% fat and 51.61% carbohydrates (13.04% w/w of composition), and citric acid (36.46% w/w of composition) were sifted through 20 mesh ASTM and mixed for 10 minutes to give a mixture. The mixture was hot melt extruded using the conditions in Table 4, cooled, milled and sifted to give the melt composite.

TABLE 4

Hot melt extruder conditions for processing of example 3
Temperature of Chambers

| Chamber | Temperature (° C.) |
| --- | --- |
| 2 | 25 |
| 3 | 40 |
| 4 | 90 |
| 5 | 160 |
| 6 | 180 |
| 7 | 180 |
| 8 | 180 |
| Die Zone | 180 |

Extruder RPM = 75
Feeder RPM = 15

Mannitol 200 SD (16.83% w/w of composition) and colloidal silica (2.0% w/w of composition) were sifted through 30 mesh ASTM. The melt composite was blended with the sifted mannitol and colloidal silica in a blender for 10 minutes to give the melt composite composition. The melt composite composition equivalent to 50 mg of curcuminoids was filled in HPMC capsules of size 00.

Example 5

Curcuminoid extract (containing 95.4% curcuminoids) (42.08% w/w of composition), mannitol (SD 200) (14.0% w/w of composition), rice bran extract containing 14.16% protein, 16.48% fat and 51.61% carbohydrates (13.04% w/w of composition), and citric acid (28.88% w/w of composition) were sifted through 30 mesh ASTM and mixed for 10 minutes to give a mixture. The mixture was hot melt extruded using the conditions in Table 4, cooled, milled and sifted to give the melt composite. Colloidal silica (2.0% w/w of composition) was sifted through 40 mesh ASTM. The melt composite was blended with the sifted colloidal silica in a blender for 10 minutes to give the melt composite composition. The melt composite composition equivalent to 50 mg of curcuminoids was filled in HPMC capsules of size 00.

Dissolution Studies:

Curcuminoid extract 95.4%, melt composite compositions of examples 3, 4 and 5 and physical mixture of example 3, all equivalent to 50 mg of curcuminoids, were analyzed for dissolution of curcuminoids at conditions mentioned earlier. The results of the same are given in Table 5.

TABLE 5

Dissolution of curcuminoid extract, melt composite compositions
of examples 3, 4 and 5, and physical mixture (PM) of example 3

| | % Cumulative Dissolution Profile | | | | |
| --- | --- | --- | --- | --- | --- |
| Time (min) | Curcuminoid Extract | PM of Ex. 3 | Ex. 3 | Ex. 4 | Ex. 5 |
| 15 | 18 | 15 | 86 | 85 | 77 |
| 30 | 27 | 20 | 89 | 88 | 83 |
| 45 | 33 | 30 | 90 | 89 | 87 |
| 60 | 38 | 30 | 92 | 89 | 88 |

* Ex. = Example; min = minutes

The dissolution data in table 5 shows:

At 15 minutes, the melt composites of examples 3, 4 and 5 exhibit a dissolution of 77%-86% when compared to a mere 15%-18% for curcuminoid extract and physical mixture At 30 minutes, the melt composite of examples 3, 4 and 5 exhibit a dissolution of 83%-88% when compared to a mere 20%-27% for curcuminoid extract and physical mixture Table 5 clearly indicates that melt composite compositions of the present invention comprising curcuminoid extract, and a mixture of mannitol and rice bran extract, exhibit a significantly higher rate and extent of dissolution, when compared to either curcuminoid extract or physical mixture.

Example 6

Curcuminoid extract (containing 95% curcuminoids) (63.15% w/w of composition), maltodextrin (Glucidex 12 D) (21.01% w/w of composition), rice bran extract containing 14.16% protein, 16.48% fat and 51.61% carbohydrates (13.84% w/w of composition) were sifted through 60 mesh ASTM and mixed for 10 minutes to give a mixture. The mixture was hot melt extruded using the conditions in Table 4, cooled, milled and sifted to give the melt composite. Colloidal silica (2.0% w/w of composition) was sifted through 40 mesh ASTM. The melt composite was blended with the sifted colloidal silica in a blender for 10 minutes to give the melt composite composition. The melt composite composition equivalent to 50 mg of curcuminoids was filled in HPMC capsules of size 00.

TABLE 6

Hot melt extruder conditions for processing of example 6
Temperature of Chambers

| Chamber | Temperature (° C.) |
| --- | --- |
| 2 | 25 |
| 3 | 40 |
| 4 | 190 |
| 5 | 190 |
| 6 | 190 |
| 7 | 190 |
| 8 | 190 |
| Die Zone | — |

Feeder RPM = 25
Extruder RPM = 100

Example 7

Curcuminoid extract (containing 95% curcuminoids) (63.15% w/w of composition) and maltodextrin (Glucidex 12 D) (34.85% w/w of composition), were sifted through 60 mesh ASTM and mixed for 10 minutes to give a mixture. The mixture was hot melt extruded using the conditions in Table 6, cooled, milled and sifted to give the melt composite. Colloidal silica (2.0% w/w of composition) was sifted through 40 mesh ASTM. The melt composite was blended with the sifted colloidal silica in a blender for 10 minutes to give the melt composite composition. The melt composite composition equivalent to 50 mg of curcuminoids was filled in HPMC capsules of size 00.

A physical mixture of the melt composite of Example 7 was prepared by sifting the individual ingredients (curcuminoid extract and maltodextrin) through 20 mesh ASTM and blending them for 10 minutes.

Dissolution Studies:

Curcuminoid extract 95.0%, melt composite compositions of examples 6 and 7 and physical mixture of example 7, all equivalent to 50 mg of curcuminoids, were analyzed for dissolution of curcuminoids at conditions mentioned earlier. The results of the same are given in Table 7.

TABLE 7

Dissolution of curcuminoid extract, melt composite compositions of examples 6 and 7 and physical mixture (PM) of example 7

| | % Cumulative Dissolution Profile | | | | |
|---|---|---|---|---|---|
| Time (min) | Curcuminoid Extract | PM of Ex 6 | PM of Ex. 7 | Ex. 6 | Ex. 7 |
| 15 | 18 | 31 | 33 | 85 | 54 |
| 30 | 27 | 34 | 40 | 91 | 67 |
| 45 | 33 | 36 | 45 | 93 | 72 |
| 60 | 38 | 42 | 43 | 93 | 75 |

* Ex. = Example; min = minutes

The dissolution data in table 7 shows,

At 15 minutes, the melt composites of example 6 comprising combination of rice bran extract and maltodextrin as carrier, exhibits significantly rapid dissolution of 86% when compared to a mere 33% and 54% for physical mixture and melt composite comprising maltodextrin alone as a carrier.

At 30 minutes, the melt composite of examples 6 exhibits a dissolution of 91% when compared to a mere 40%-67% for physical mixture and melt composite comprising maltodextrin alone as a carrier.

Table 7 clearly indicates that melt composite compositions of the present invention comprising curcuminoid extract and maltodextrin as a carrier, or mixture of carriers such as maltodextrin and rice bran extract, exhibit a significantly rapid dissolution, when compared to their physical mixture as well as curcuminoid extract.

Example 8

Curcuminoid extract (containing 95% curcuminoids) (42.15% w/w of composition), maltodextrin (Glucidex 12 D) (14.01% w/w of composition), rice bran extract containing 14.16% protein, 16.48% fat and 51.61% carbohydrates (13.84% w/w of composition) and mannitol (SD 200) (28.0% w/w of composition) were sifted through 60 mesh ASTM and mixed for 10 minutes to give a mixture. The mixture was hot melt extruded using the conditions in Table 6, cooled, milled and sifted to give the melt composite. Colloidal silica (2.0% w/w of composition) was sifted through 40 mesh ASTM. The melt composite was blended with the sifted colloidal silica in a blender for 10 minutes to give the melt composite composition. The melt composite composition equivalent to 50 mg of curcuminoids was filled in HPMC capsules of size 00.

A physical mixture of the melt composite of Example 8 was prepared by sifting the individual ingredients (curcuminoid extract, maltodextrin, rice bran extract and mannitol) through 20 mesh ASTM and blending them for 10 minutes.

Example 9

Curcuminoid extract (containing 95% curcuminoids) (42.15% w/w of composition), maltodextrin (Glucidex 12 D) (27.85% w/w of composition), and mannitol (SD 200) (28.0% w/w of composition) were sifted through 60 mesh ASTM and mixed for 10 minutes to give a mixture. The mixture was hot melt extruded using the conditions in Table 6, cooled, milled and sifted to give the melt composite. Colloidal silica (2.0% w/w of composition) was sifted through 40 mesh ASTM. The melt composite was blended with the sifted colloidal silica in a blender for 10 minutes to give the melt composite composition. The melt composite composition equivalent to 50 mg of curcuminoids was filled in HPMC capsules of size 00.

A physical mixture of the melt composite of Example 8 was prepared by sifting the individual ingredients (curcuminoid extract, maltodextrin, rice bran extract and mannitol) through 20 mesh ASTM and blending them for 10 minutes.

Dissolution Studies:

Curcuminoid extract 95.0%, melt composite compositions of examples 8 and 9 and physical mixtures of both the examples, all equivalent to 50 mg of curcuminoids, were analyzed for dissolution of curcuminoids at conditions mentioned earlier. The results of the same are given in Table 8.

TABLE 8

Dissolution of curcuminoid extract, melt composite compositions of examples 8 and 9 and physical mixtures (PM) of example 8 and 9

| | % Cumulative Dissolution Profile | | | | |
|---|---|---|---|---|---|
| Time (min) | Curcuminoid Extract | PM of Ex 8 | PM of Ex. 9 | Ex. 8 | Ex. 9 |
| 15 | 18 | 33 | 31 | 83 | 86 |
| 30 | 27 | 36 | 34 | 84 | 88 |
| 45 | 33 | 41 | 39 | 84 | 89 |
| 60 | 38 | 43 | 40 | 85 | 90 |

At 15 minutes, the melt composites of example 8 comprising combination of rice bran extract, maltodextrin and mannitol as carrier, exhibits significantly rapid dissolution of 83% when compared to mere 33% for physical mixture. Similarly melt composite of example 9 comprising mixture of maltodextrin and mannitol as carrier, exhibits significantly rapid dissolution of 86% as compared to the physical mixture.

At 30 minutes, the melt composite of example 8 and 9 exhibit a dissolution of 84% and 88% respectively, when compared to dissolution of mere 34 to 36% for physical mixtures of both the compositions.

Table 8 clearly indicates that melt composite compositions of the present invention comprising curcuminoid extract and mixture of either rice bran extract, maltodextrin and mannitol as a carrier, or mixture of maltodextrin and mannitol as a carrier, exhibit a significantly higher rate and extent of dissolution, when compared to their physical mixtures as well as curcuminoid extract.

Example 10

Curcuminoid extract (containing 95% curcuminoids) (89.46% w/w of composition) and mannitol (SD 200) (10.54% w/w of composition) were sifted through 60 mesh ASTM and mixed for 10 minutes to give a mixture. The mixture was hot melt extruded using the conditions in Table 6, cooled, milled and sifted to give the melt composite. The melt composite composition equivalent to 50 mg of curcuminoids was filled in HPMC capsules of size 00.

Dissolution Studies:

Curcuminoid extract 95.0%, melt composite composition of example 10, equivalent to 50 mg of curcuminoids, was analyzed for dissolution of curcuminoids at conditions mentioned earlier. The results are given below.

TABLE 9

Dissolution of curcuminoid extract and melt composite composition of example 10

| Time | % Cumulative Dissolution Profile | |
|---|---|---|
| (min) | Curcuminoid Extract | Example 10 |
| 15 | 18 | 69 |
| 30 | 27 | 71 |
| 45 | 33 | 73 |
| 60 | 38 | 75 |

Table 9 clearly indicates that melt composite compositions of the present invention comprising mannitol as a carrier, exhibits a significantly higher rate and extent of dissolution, when compared to curcuminoid extract.

Example 11: Pharmacokinetic Studies

The pharmacokinetics of curcuminoid melt composites of the present invention were studied following a single oral administration of melt composite compositions of examples 4 and 5, in comparison with curcuminoid extract (active). The study was conducted in male Sprague Dawley rats. Animals were orally administered with melt composite compositions of examples 4 and 5, and curcuminoid extract containing 95.4% curcuminoids, each at a dose equivalent to 300 mg/kg of body weight. Blood samples were collected at 0 (pre dose), 0.50, 1, 2, 4, 6, 8, 12, 16 and 24 hours. Plasma samples were analyzed for $C_{max}$, AUC and $T_{max}$. Table 10 gives the results of the pharmacokinetic data.

TABLE 10

Pharmacokinetic data

| Parameter | Curcuminoid Extract | Ex. 3 | Ex. 4 |
|---|---|---|---|
| Curcumin (Mean) | | | |
| $C_{max}$ (ng/ml) | 102.355 | 410.024 | 442.411 |
| $AUC_{0-24}$ (h*ng/ml) | 381.086 | 1943.500 | 2161.167 |
| $T_{max}$ (h) | 5.40 | 3.58 | 2.17 |
| Total Curcuminoids (Mean) | | | |
| $C_{max}$ (ng/ml) | 123.99 | 445.903 | 484.952 |
| $AUC_{0-24}$ (h*ng/ml) | 454.416 | 2104.167 | 2438.667 |
| $T_{max}$ (h) | 5.20 | 3.58 | 2.75 | ng = nanogram;
pg = picogram;
ml = milliliter;
hrs = hours

The in-vivo data in Table 10 shows:
- administration of compositions of the present invention comprising melt composites results in a $C_{max}$ of curcumin of 410.024 ng/ml and 442.411 ng/ml which is 4.0-4.3 times the $C_{max}$ of curcumin from curcuminoid extract (102.355 ng/ml)
- administration of the present invention comprising melt composites results in a $C_{max}$ of total curcuminoids of 445.903 ng/ml and 484.952 ng/ml which is 3.6-3.9 times the $C_{max}$ of total curcuminoids from curcuminoid extract (123.99 ng/ml)
- administration of compositions of the present invention comprising melt composites results in a $AUC_{0-24}$ of curcumin of 1943.500 h*ng/ml and 2161.167 h*ng/ml which is 5.1-5.7 times the $AUC_{0-24}$ of curcumin from curcuminoid extract (381.086 h*ng/ml)
- administration of compositions of the present invention comprising melt composites results in a $AUC_{0-24}$ of total curcuminoids of 2104.167 h*ng/ml and 2438.667 h*ng/ml which is 4.6-5.4 times the $AUC_{0-24}$ of total curcuminoids from curcuminoid extract (454.416 h*ng/ml)
- administration of compositions of the present invention comprising melt composites results in an early onset on action with a $T_{max}$ of 3.58 hours and 2.75 hours when compared to $T_{max}$ of curcuminoid extract (5.2 hours)

Table 10 clearly indicates that the compositions of the present invention, after oral administration, exhibit better oral bioavailability, measured as the area-under-the-curve $(AUC_{0-24})$ with respect to curcumin and total curcuminoids, in blood plasma, when compared to curcuminoid extract.

The time to reach maximum plasma concentrations $(T_{max})$ values and the maximum plasma concentrations $(C_{max})$ values, clearly indicate that curcumin and total curcuminoids, from the compositions of the present invention, exhibit an early onset of action and higher rate of absorption into the blood when compared to curcuminoid extract.

Example 12: Bioavailability Study

An open label, randomized, cross-over, single oral dose comparative pharmacokinetic study of Curcuminoid composite Capsules (containing 150 mg of curcuminoids) (Test) was conducted with Standard turmeric extract Capsules 95% (containing 500 mg of curcuminoids) (Reference) of Synthite Industries (P) Ltd in normal healthy adult human subjects under fasting conditions.

14 subjects aged between 18 and 45 years were enrolled in the study, who were instructed to have all meals free of turmeric and black pepper and any marketed spice mixtures containing turmeric and/or black pepper. After an overnight fasting of 10 hours prior to scheduled time of dosing, as per randomization schedule, test (1×150 mg) or reference (3×500 mg) product was administered with 240 mL of water at ambient temperature under fasting condition.

The Plasma concentrations of the analytes like total curcumin and total curcuminoids were measured using validated Liquid Chromatography-Mass Spectroscopy/Mass Spectroscopy (LC-MS/MS) bioanalytical method. Comparative evaluation of the Cmax and $AUC_{0-t}$ values for Total Curcuminoids as well as Total Curcumin of the test formulation (Melt composite) and reference formulation (Curcuminoid extract) as captured in Table 11.

TABLE 11

Relative absorption and relative bioavailability
Relative Absorption & Relative bioavailability of the Formulations [Test (T) Vs. Reference (R)]

| | Parameter | Test (Geometric Least Square Mean) | Reference (Geometric Least Square Mean) | Relative absorption | Relative bioavailability |
|---|---|---|---|---|---|
| Total Curcuminoids | $C_{max}$ | 97.804 | 49.251 | 19.858 | |
| | $AUC_{0-t}$ | 475.176 | 496.212 | | 9.576 |
| | $AUC_{0-inf}$ | 481.372 | 562.223 | | |
| Total Curcumin | $C_{max}$ | 53.117 | 21.603 | 24.588 | |
| | $AUC_{0-t}$ | 256.171 | 203.573 | | 12.584 |
| | $AUC_{0-inf}$ | 361.082 | 372.922 | | |

TABLE 11-continued

Relative absorption and relative bioavailability
Relative Absorption & Relative bioavailability of
the Formulations [Test (T) Vs. Reference (R)]

| | Parameter | Test (Geometric Least Square Mean) | Reference (Geometric Least Square Mean) | Relative absorption | Relative bioavailability |
|---|---|---|---|---|---|
| Tetrahydro-curcumin | Cmax | 177.144 | 79.872 | 22.178 | |
| | AUC0-t | 1273.923 | 821.847 | | 15.501 |
| | AUC0-inf | 1461.895 | 1252.295 | | |

For Total Curcuminoids, the Geometric LSM of $C_{max}$ for the test formulation (T) was 97.804 ng/ml whereas for the reference formulation (R), it was 49.251 ng/ml. Based on these values, for total curcuminoids, the test formulation (T) was observed to yield 19 times higher relative absorption as compared to the reference formulation (R).

For Total Curcuminoids, the Geometric LSM of $AUC_{0-t}$ for test formulation (T) was 475.176 ng·hr/mL, whereas for the reference formulation (R), it was 496.212 ng·hr/ml. Based on these values, for total curcuminoids, the test formulation (T) was found to have 9.5 times higher relative bioavailability than the reference formulation (R).

For Total Curcumin, the Geometric LSM of $C_{max}$ for the test formulation (T) was 53.117 ng/mL whereas for the reference formulation (R), it was 21.603 ng/ml. Based on these values, for total curcumin, the test formulation (T) was observed to yield 25 times higher relative absorption as compared to the reference formulation (R).

For Total Curcumin, the Geometric LSM of $AUC_{0-t}$ for test formulation (T) was 256.171 ng·hr/mL, whereas for the reference formulation (R), it was 203.573 ng·hr/ml. Based on these values, for total curcumin, the test formulation (T) was found to have 13 times higher relative bioavailability than the reference For Tetrahydrocurcumin, the Geometric LSM of $C_{max}$ for the test formulation (T) was 177.1444 ng/mL whereas for the reference formulation (R), it was 79.8723 ng/ml. Based on these values, for tetrahydrocurcumin, the test formulation (T) was observed to yield 22 times higher relative absorption as compared to the reference formulation (R).

For tetrahydrocurcumin, the Geometric LSM of $AUC_{0-t}$ for test formulation (T) was 1273.9233 ng·hr/mL, whereas for the reference formulation (R), it was 821.8471 ng·hr/mL. Based on these values, for tetrahydrocurcumin, the test formulation (T) was found to have 16 times higher relative bioavailability than the reference formulation (R).

Based on pharmacokinetic and statistical analysis, melt composite of the invention in the dose of 150 mg of actives was found to have higher relative absorption and about 10 to 15 times superior relative bioavailability as compared to the Standard turmeric extract Capsules 95% in the dose of 1500 mg of actives.

The invention claimed is:

1. A melt composite comprising one or more curcuminoids and a carrier, wherein the melt composite is prepared by melt granulation, melt extrusion, melt solidification, or melt spray congealing, wherein the melt composite does not include a synthetic polymer or a thermoplastic polymer, wherein the carrier is a mixture of maltodextrin and rice bran extract, and the ratio of the one or more curcuminoids to the mixture of rice bran extract and maltodextrin ranges from about 1:0.1 to about 1:20.

2. The melt composite as claimed in claim 1, wherein the ratio of the one or more curcuminoids, rice bran extract and maltodextrin ranges from 1:0.05:0.1 to 1:10:10.

3. The melt composite as claimed in claim 1, wherein the melt composite further comprises at least one or more excipients selected from diluents, binders, disintegrants, lubricants, glidants, solubilizers, vehicles, stabilizers, buffers, sorbents, antioxidants, complexing agents, viscosity enhancers, plasticizers, coating materials, sweeteners, colours, flavors or a combination thereof.

4. A process for preparing a melt composite according to claim 1, the process comprising
  (a) mixing one or more curcuminoids and a carrier, wherein the carrier is a mixture of maltodextrin and rice bran extract;
  (b) subjecting the mixture of the one or more curcuminoids and the carrier of step (a) to heat treatment to obtain a molten mass;
  (c) extruding the molten mass of step (b) to obtain extrudates;
  (d) optionally adding one or more excipients to the extrudates of step (c); and
  (e) cooling and milling the resulting extrudates to obtain the melt composite,
wherein the melt composite does not include a synthetic polymer or a thermoplastic polymer.

5. The process of claim 4, wherein steps (b) and (c) comprise hot melt extruding the mixture of the one or more curcuminoids and the carrier to form a hot melt extrudate.

6. The melt composite of claim 1, wherein the maltodextrin in the mixture fpr the carrier is obtained from a natural source.

7. The melt composite as claimed in claim 1, wherein the melt composite comprises about 5 to about 90% by weight of the one or more curcuminoids.

* * * * *